US00PP08285P

United States Patent [19]

Trees

[11] Patent Number: Plant 8,285

[45] Date of Patent: Jun. 29, 1993

[54] GERANIUM PLANT — BSR-232 LIGHT SCARLET CULTIVAR

[75] Inventor: Scott C. Trees, Arroyo Grande, Calif.

[73] Assignee: George J. Ball, Inc., West Chicago, Ill.

[21] Appl. No.: 761,704

[22] Filed: Sep. 18, 1991

[51] Int. Cl.[5] ..... A01H 5/00

[52] U.S. Cl. ..... Plt./87.12

[58] Field of Search ..... Plt./87.12

[56] References Cited

U.S. PATENT DOCUMENTS

P.P. 5,933 4/1987 Schumann ..... Plt. 87.12

*Primary Examiner*—James R. Feyrer
*Assistant Examiner*—Elizabeth F. McElwain
*Attorney, Agent, or Firm*—Burns, Doane, Swecker & Mathis

[57] ABSTRACT

A new and distinct tetraploid *Pelargonium*×*hortorum* cultivar named BSR-232 Light Scarlet is provided. This new Zonal Geranium cultivar was the result of a controlled breeding program wherein an unnamed plant designated 3214B-85 was pollinated by the Tango cultivar (U.S. Plant Pat. No. 5,933). The new cultivar forms attractive semi-double light scarlet florets which contrast well with dark green distinctly zoned foliage. The attractive dark green foliage coloration is well retained even during shipment. The growth habit is inherently compact and self-branching and does not require the use of growth regulators to maintain such growth characteristic. When grown outdoors, the flowering is continuous and good heat tolerance is exhibited.

1 Drawing Sheet

SUMMARY OF THE INVENTION

The present invention comprises a new and distinct Geranium cultivar, botanically known as *Pelargonium*×*hortorum*, and hereinafter is referred to by the cultivar name BSR-232 Light Scarlet.

The new cultivar is the product of a planned breeding program which had as its objective the creation of a highly productive new Geranium cultivar which exhibits attractive blossoms, dark green foliage, a compact self-branching growth habit, no requirement for the use of a growth regulator, a propensity for rapid rooting, and stable foliage coloration during shipment. This objective was satisfactorily fulfilled in the cultivar of the present invention.

The breeding program which resulted in the production of the new cultivar of the present invention was carried out in a controlled environment during 1989 at Santa Maria, Calif., U.S.A. The female parent (i.e., the seed parent) was an unnamed plant designated 3124B-85. Such female parent formed semi-double blush florets, and formed non-zoned medium green foliage. The male parent (i.e., the pollen parent) was the Tango cultivar (U.S. Plant Pat. No. 5,933). Such male parent formed semi-double red florets, and formed dark green foliage. The parentage of the new cultivar can be summarized as follows:

3124B-85×TANGO.

The seeds resulting from the above pollination were sown and plantlets were obtained which were physically and biologically different from each other. Selective study which was finalized on Jan. 20, 1990, at Santa Maria, Calif. resulted in the identification of a single plant of the new cultivar. This plant initially was designated BSR-232.

It was found that the new cultivar of the present invention:

(a) exhibits attractive light scarlet semi-double florets,
(b) forms attractive dark green foliage which resists breakdown during shipment,
(c) bears distinctly-zoned leaves, and
(d) exhibits an inherently compact and self-branching growth habit in the absence of growth regulators.

Asexual reproduction of the new cultivar by vegetative cuttings initially taken on Feb. 10, 1990, and horticulturally examined in a controlled environment on Apr. 15, 1990, at Santa Maria, Calif., has demonstrated that the characteristics of the new cultivar as herein described are firmly fixed and are retained through successive generations of asexual propagation.

When plant material of the BSR-232 Light Scarlet cultivar is subjected to standard random amplified polymorphic DNA marker analysis (RAPD) using polymerase chain reaction (PCR) and a known unique set of DNA primers, it is found to exhibit a distinctive fingerprint map which is on file at the Ball Flora Plant Division of George J. Ball, Inc. at Arroyo Grande, Calif.

BSR-232 Light Scarlet has not been observed under all possible environmental conditions to date. Accordingly, it is possible that the phenotype may vary somewhat with variations in the environment, such as temperature, light intensity, and day length.

When the new cultivar of the present invention is compared to the Eclipse Salmon Orange cultivar (now U.S. Plant Pat. No. 7,969), the BSR-232 Light Scarlet cultivar is found to be more floriferous in field trials and to exhibit florets which are more red and less orange-red than the Eclipse Salmon Orange cultivar. Also, the puduncle at the base of the Showcase Light Scarlet cultivar is bright green while that of the Eclipse Salmon Orange cultivar is a lighter yellow-green coloration as specified in greater detail hereafter.

The new cultivar of the present invention is being marketed under the Showcase trademark.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at Santa Maria, Calif.

DETAILED DESCRIPTION

The chart used in the identification of colors described herein is The R.H.S. Colour Chart of The Royal Horticultural Society, London, England. Color terminology in common terms sometimes precedes the reference to The R.H.S. Colour Chart information. The color values were determined on Jul. 30, 1991 at 11:00 a.m. to 12:00 noon at Santa Maria, Calif. The plants described were grown under standard greenhouse conditions.

Classification:

*Botanical.*—*Pelargonium*×*hortorum*, cv. BSR-232 Light Scarlet.

*Commercial.*—Zonal Geranium.

INFLORESCENCE

A. Umbel:

*Average diameter.*—Approximately 11 to 12 cm.

*Average depth.*—Approximately 4.5 to 5.0 cm.

*Peduncle length.*—Approximately 14 to 17 cm.

*Peduncle color.*—At base Green Group 134A. This compares to Yellow-Green Group 144B for the Eclipse Salmon Orange cultivar.

*Pedicel length.*—Approximately 3 to 3.5 cm.

When five month old plants are grown in the field, the BSR-232 Light Scarlet cultivar commonly possesses approximately 52 to 57 umbels per plant while the Tango cultivar commonly possesses aproximately 45 to 50 umbels per plant, and the Eclipse Salmon Orange cultivar commonly possesses approxmately 42 to 45 umbels per plant. Such field grown plants commonly possess approximately 45 to 50 florets per umbel for the BSR-232 Light Scarlet cultivar, aproximately 60 to 65 florets per umbel for the Tango cultivar, and approximately 35 to 40 florets per umbel for the Eclipse Salmon Orange cultivar.

B. Corolla:

*Average diameter.*—Approximately 4.5 to 5.0 cm.

*Form.*—Semi-double, commonly 5 petals plus approximately 2 to 5 petaloids. There commonly are 5 large somewhat flat non-imbricate petals measuring approximately 2.3 cm. in length and approximately 2.3 cm. in width, and approximately 1 to 3 smaller petaloids ranging in length from approximately 0.6 to 0.9 cm. In contrast the florets of the Tango cultivar commonly possess approximately 5 to 6 concave large imbricate petals which measure approximately 2.2 cm. in length and approximately 2.2 cm. in width, and approximately 3 to 5 petaloids which range from approximately 1.3 to 2.0 cm. in length. The florets of the Eclipse Salmon Orange cultivar commonly possess approximately 7 to 8 large imbricate petals which are twisted and concave and measure approximately 2.4 cm. in length and approximately 1.9 cm. in width, and approximately 2 to 5 petaloids which range from approximately 0.3 to 2.0 cm. in length.

*Color (general tonality from a distance of 3 meters)*—.—Orange-Red Group 33A.

*Color (abaxial).*—Red Group 44B. This compares Orange-Red Group 33B for the Eclipse Salmon Orange cultivar.

*Color (adaxial).*—Orange-Red Group 33A. This compares to Orange-Red Group 32A for the Eclipse Salmon Orange cultivar. The petals of the BSR-232 Light Scarlet cultivar lack an eye in contrast to those of the Tango cultivar which do possess an eye.

C. Bud

*Shape.*—Upright, in a hemispheroidal cluster.

*Color (abaxial).*—Red Group 44B.

*Color (adaxial).*—Orange-Red Group 33A.

D. Reproductive organs

*Androecium.*—The anthers commonly are approximately 2.5 to 3.0 mm. in length. The pollen is orange in coloration, Orange-Red Group 30A; and the filaments tend to be straight, and sometimes are petaloid in nature.

*Gynoecium.*—The pistil length commonly is approximately 9 to 10 mm., there is a single stigma which commonly branches into 5 or 6 parts above the style, and the style length is approximately 4.5 to 5.0 mm.

*Fertility.*—The BSR-232 Light Scarlet and Eclipse Salmon Orange cultivars commonly do not set fruit in the field without manual pollination.

E. Spring flowering response period: Approximately 6 to 7 weeks from rooted cuttings under greenhouse conditions maintained at 55° F. at night and 72° F. during the day when potted on March 1st in a soil mix (e.g., Sunshine No. 2 brand soil mix) in 10 cm. pots.

F. Outdoor flower production: Is more floriferous than Eclipse Salmon Orange in field trials, is continuous flowering, and exhibits good heat tolerance.

G. Durability: The dark green foliage coloration is relatively stable and is tolerant to stresses induced by shipping with the absence of any substantial foliar breakdown.

PLANT

A. Foliage: Darker zoning appears at about one-third the distance from the leaf edge to the leaf pedicel.

*Form.*—Reniform, cordate base. However, the zoning of the BSR-232 Light Scarlet cultivar is not particularly distinct and is unlike that of the Eclipse Salmon Orange cultivar which commonly does exhibit a distinct dark zone.

*Margin.*—Slightly crenate.

*Color (abaxial).*—Dark green, Green Group 132A.

*Color (adaxial).*—Medium green, Yellow-Green Group 137B.

*Color (zonation).*—Dark green, Green Group 135A.

*Susceptibility to Botrytis blight.*—Some tolerance.

B. General appearance and form:

*Internode length.*—Commonly varies from approximately 2.5 to 4.0 cm.

*Branching pattern.*—Freely basal branching. The BSR-232 Light Scarlet cultivar is more compact in its growth habit than the Tango and Eclipse Salmon Orange cultivars. The BSR-232 Light Scarlet cultivar does not require pinching or a growth regulator to produce a well-branched plant. However, the Eclipse Salmon Orange cultivar commonly does require either pinching or a growth regulator to produce a well-branched plant.

*Height.*—Approximately 20 to 25 cm. above a 10 cm. pot when the blossoms first open.

I claim:

1. A new and distinct cultivar of Geranium plant named BSR-232 Light Scarlet, substantially as herein shown and described, which:

(a) exhibits attractive light scarlet semi-double florets,
(b) forms attractive dark green foliage which resists breakdown during shipment,
(c) bears distinctly-zoned leaves, and
(d) exhibits an inherently compact and self-branching growth habit in the absence of growth regulators.

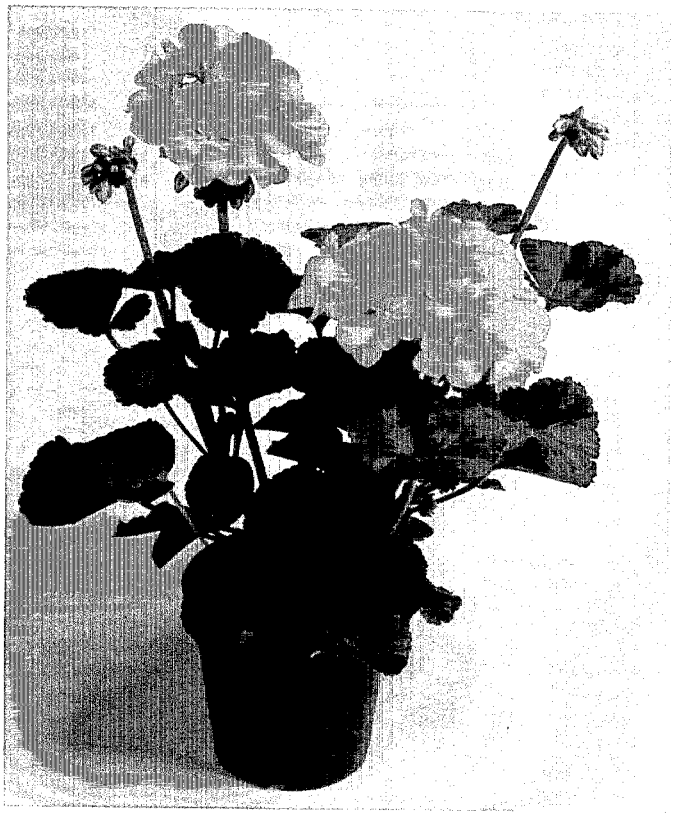

* * * * *